United States Patent
Hunt

[19]

[11] Patent Number: 6,053,169
[45] Date of Patent: Apr. 25, 2000

[54] MEDICAL STRAP FOR TREATING INJURED PATIENT

[76] Inventor: Dermot A. Hunt, 250 Fairfield Ct., Palatine, Ill. 60067

[21] Appl. No.: 09/255,425

[22] Filed: Feb. 22, 1999

[51] Int. Cl.[7] .................................................. A61B 19/00
[52] U.S. Cl. ............................... 128/876; 2/338; 128/878
[58] Field of Search .......................... 602/5, 19; 128/869, 128/876, 878; 2/331, 338

[56] References Cited

U.S. PATENT DOCUMENTS

| | | | |
|---|---|---|---|
| 70,238 | 10/1867 | McCoy | 2/338 |
| 2,503,157 | 4/1950 | Knee | 2/338 |
| 2,847,746 | 8/1958 | Freeman | 2/338 |
| 4,545,370 | 10/1985 | Welsh | 2/338 |

Primary Examiner—Michael A. Brown
Attorney, Agent, or Firm—Charles F. Lind

[57] ABSTRACT

The disclosed medical device having an elongated strap sized to fit around a patient's body area with overlapping opposite under and outer layer strap ends, and with an inside strap face then lying proximate the patient and an opposite outside face. A lever is pivoted relative to the outside face of the under layer strap end and stops are formed at locations along the lever spaced from the lever pivot. The outer layer strap end has openings therein spaced apart along the strap. After wrapping the device loosely around a patient's body area, the lever is fitted through any selected strap opening to establish engagement of a respective stop-opening combination for interlocking the lever and strap together and defining an endless band encircling the patient's body area. The lever can then be pivoted toward the strap outer layer end to reduce the band circumference to a desired size and tightness, and then held relative to the strap in this closed position.

9 Claims, 3 Drawing Sheets

6,053,169

MEDICAL STRAP FOR TREATING INJURED PATIENT

BACKGROUND OF THE INVENTION

When a person sustains a flesh cut, wound or bone break on an arm, leg, or even on the head or body torso (all frequently noted as a limb herein), it is wise if not imperative to medically treat the matter as soon as possible, if even on an emergency or temporary basis. This would include stopping excessive bleeding from the wound or splinting and immobilizing a limb due to possible broken bone structure therein. However, overall hostile environments or accident situations (war-time battlefield or crashed vehicle, etc.) might make reaching, moving or working on the patient difficult; and the patient might be unconscious or otherwise incapable of offering assistance. Some form of a strap device has conventionally been used to wrap around the patient's limb for effectively: (1) holding a wound dressing in place, or (2) serving as a compress to reduce bleeding, or (3) serving as a tourniquet is restricting severe bleeding; however, such devices have traditionally been quite single purposed and incapable of selectively achieving all such functions.

SUMMARY OF THE INVENTION

This invention relates to an improved medical strap device, suited for use primarily in an emergency or temporary mode and/or in restricted or hostile environments, for being wrapped around and over an injured body limb for treating the injury.

One object of this invention is to provide a medical strap device that might be secured in place on patients of vastly different sizes and/or limb locations, and with selected degrees of tightness or applied pressure, for purposes including: (1) merely overlying and holding with mild pressures a dressing over the injured area, (2) overlying the injured area with increased pressures to serve as a compress for stopping bleeding, or (3) overlying the injured limb with great pressures to serve as a tourniquet in attempting to stop severe bleeding from the wound.

Another object of this invention is to provide additional structures that can be used with several of the above mentioned medical strap devices, for forming an emergency splinting fixture spanning possible broken bones in the patient.

BRIEF DESCRIPTION OF THE DRAWINGS

Specific objects, features or advantages of the invention will be more fully understood and appreciated after consideration of the following description of the invention, which includes as a part thereof the accompanying drawings, wherein.

DETAILED DESCRIPTION OF THE INVENTION

Figure 3:
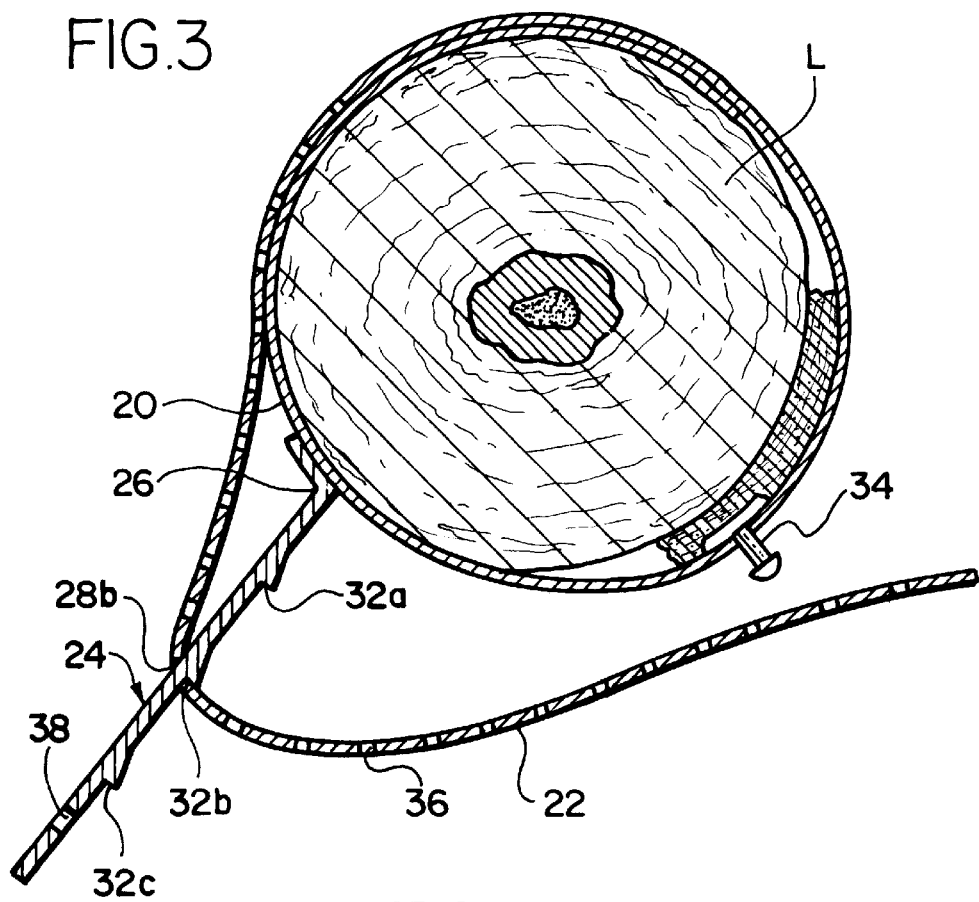
FIGS. 3 and 4 are sectional like views, as seen generally from line 4—4 in FIG. 1, showing the medical strap device respectively in an intermediate position being secured on the arm, and in a final position tightened on the arm.
Figure 4:
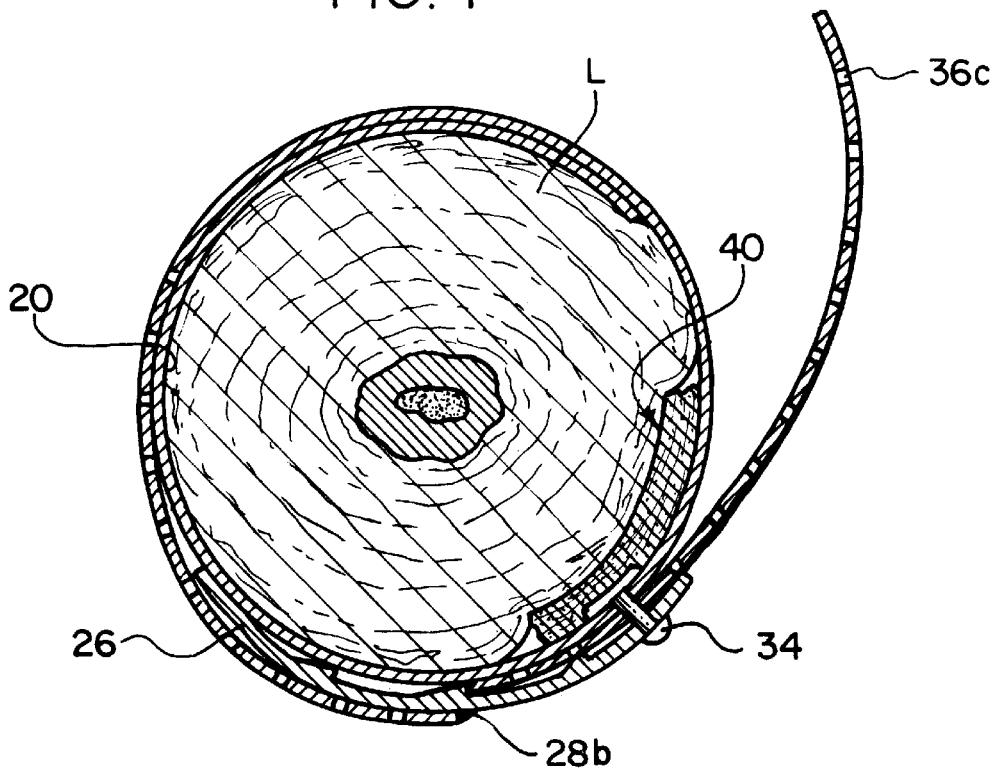
Figure 5:
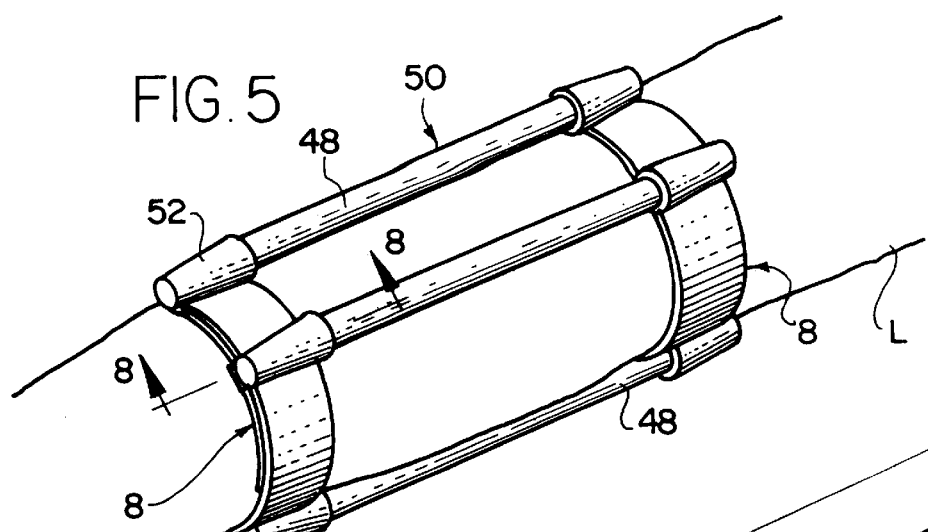
FIG. 5 is a perspective view of a patient's arm, with two inventive straps secured thereon, in the nature of a splint.
Figure 7:
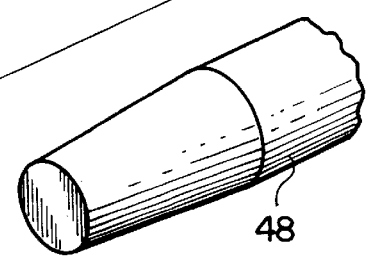
FIG. 7 is a perspective view of the opposite clip component used in the splint apparatus of FIG. 5.
Figure 6:
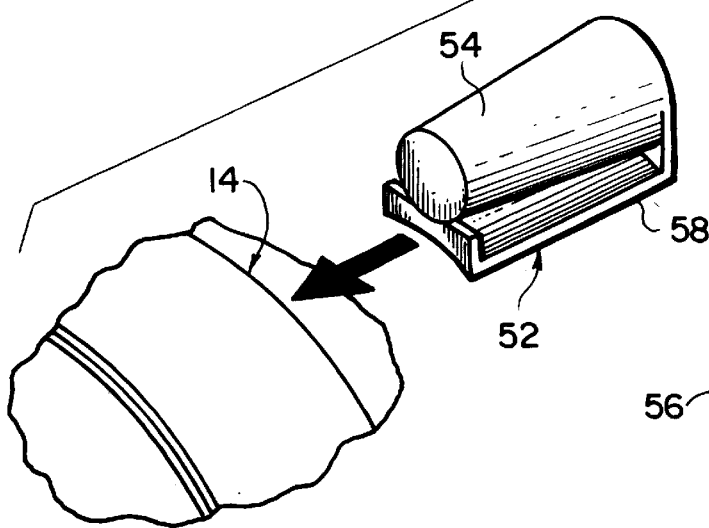
FIG. 6 is a exploded perspective view of one of the clip and rod components, and one adjacent strap component used in the splint apparatus of FIG. 5.
Figure 8:
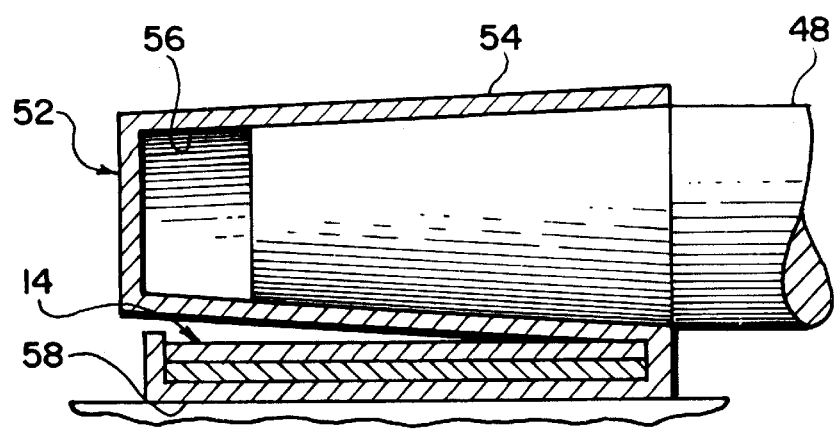
FIG. 8 is a sectional view as seen from line 8—8 in FIG. 5.

This invention provides a medical band device 8 comprised of an elongated strap 10 that is sized to fit around the patient's body area proximate an injury, with strap ends overlapping and with apparatus 12 in the region of overlap for securing the strap ends together and for then defining an endless band 14 (FIGS. 3 and 4) connected around the patient and for tightening the endless band 14 to any of several selected degrees of tightness. Typically, the strap 10 can be wound around a limb such as a leg or arm although it could be used around the body torso or even the head, and it might most commonly overlie and hold in place a dressing covering the wounded area.

For ease in disclosing the medical device 8, its construction will be referenced to how it normally will be secured on the patient's body. For example, when the strap 10 is wound around the patient, there will be an inside strap face 16 against or proximate the patient and an opposite outside face 18, and the strap ends in the area of overlapping will have an under layer end 20 proximate the patient and an outer layer end 22 overlying the outside face 18 of the under layer end 20.

Projecting from the outside face 18 of the strap under layer end 20, a preferred embodiment of the device will have a lever 24 pivoted as at 26 relative to the strap, to swing about an axis disposed substantially perpendicular to the elongated axis of the strap. The strap will have many openings 28 generally (and 28a, 28b, 28c, etc. specifically) substantially equally spaced apart (such as possibly a distance of between one centimeter and one inch) along the strap toward a strap outer layer end 22 with the first opening 28a being spaced from the lever pivot 26 by a distance slightly exceeding the length of the lever 24.

The lever 24 will further have intermediate its ends different stops 32 generally (and 32a, 32b, 32c, etc specifically) spaced apart at different spacings from the lever pivot 26, the stops preferably being formed on the side of the lever facing the strap outer layer end 22. The lever 24 is adapted to be fitted into any of the openings 28 until a desired stop 32 engages and becomes held fast against the inside strap face 16, as will more fully be noted later, operable to set the size and tightness of the band 10 when securing the medical device 8 on the patient.

A post or pin 34 will further project away from the outside face 18 of the strap, at a location spaced from the lever pivot 26 by a distance slightly less than the length of the lever 24. The lever 24 further will have at a corresponding spacing from the lever pivot 26 an opening 38 suited to be fitted over and become interlocked with the post 34.

The strap 10 might further have equally spaced openings 36 generally (or 36a, 36b, 36c, etc. specifically) each sized to fit over the post 34, these openings being approximately centered laterally of the strap and midway between each adjacent pair of the lever-receiving openings 28. The first post-receiving opening 36a might be spaced from the first lever-receiving opening 28a in the direction remotely of the lever pivot 26 a distance generally corresponding to the space between the lever pivot 26 and the locking post 34, and the last opening 36c correspondingly might be spaced beyond the last opening 28c by this same distance.

Figure 1:
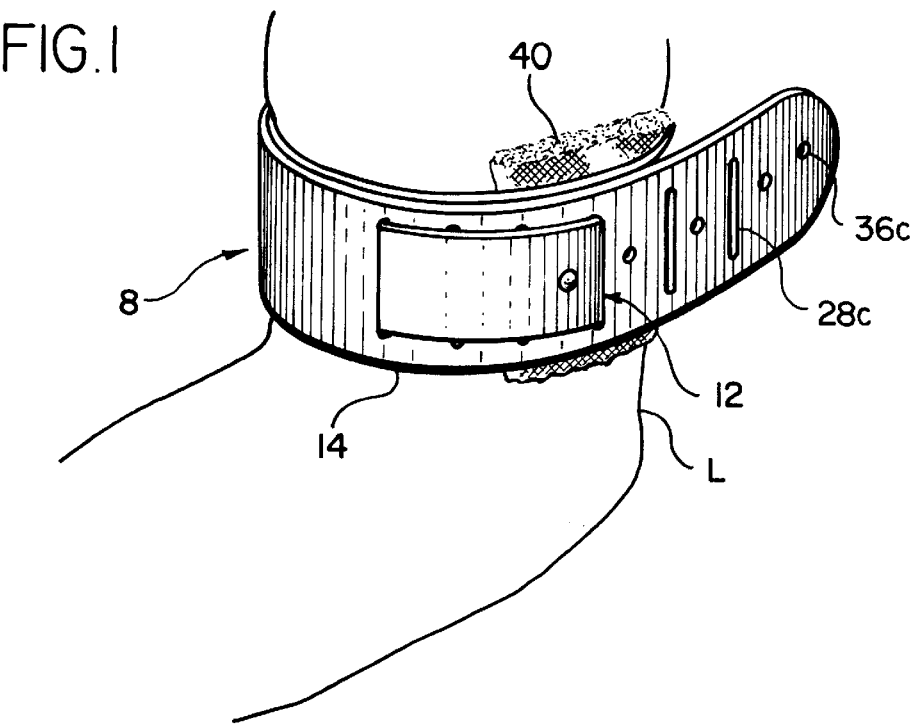
FIG. 1 is a perspective view of the inventive medical strap device shown wrapped in place over a wounded area on a patient's arm.
Figure 2:
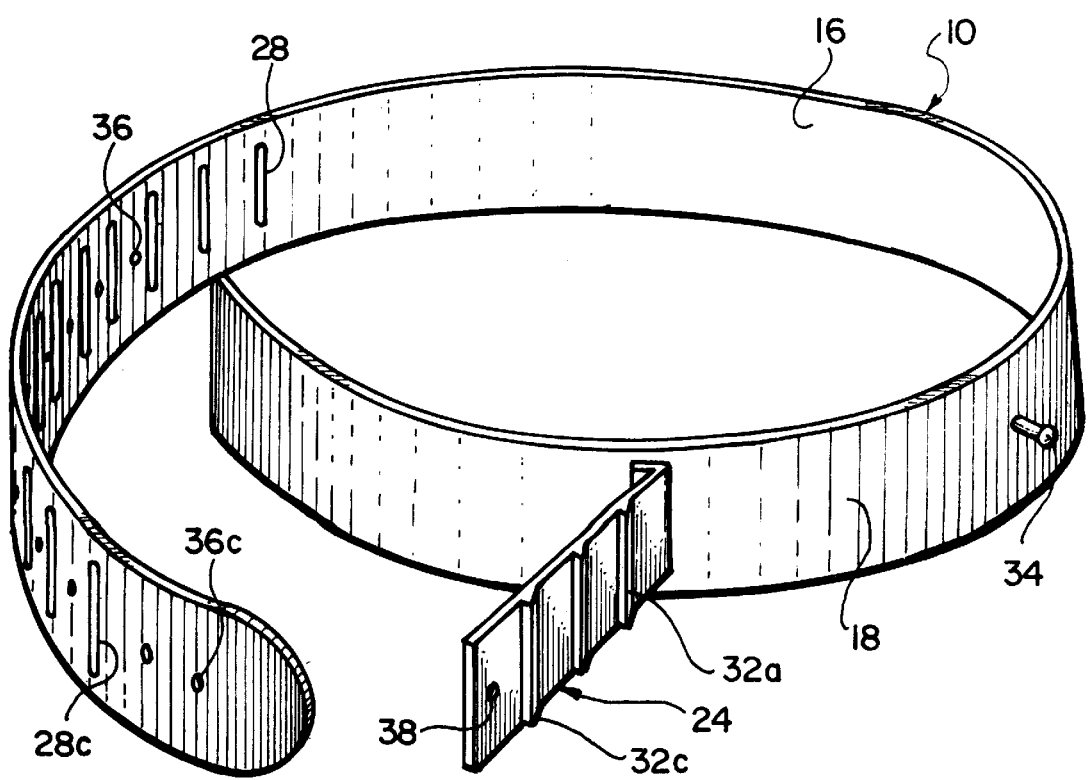
FIG. 2 is a perspective view of the inventive medical strap device, shown it partly coiled as it might be before being used.

The medical device 8 typically would be applied to a patient's limb "L" (illustrated as an arm in FIGS. 1, 3 and 4) after any dressing 40 or the like is placed over a local injured area or wound, with an intermediate portion of the strap being positioned to overlie the dressing and with the under layer end 20 and outer layer end 22 then being spaced on opposite sides of the wound. The strap ends are further wound around the patient's limb until overlapped, whereupon the lever 24 can then be fitted through an appropriate lever-receiving opening 28 spaced along the strap. This would be achieved by pivoting the lever in the direction toward the inner layer end 20 and inserting the free lever end into the selected opening while that part of the strap is yet radially spaced from the outside face 18 of the strap under layer end.

Both the lever 24 and lever-receiving openings 28 might be sized and laterally elongated, so that upon slight manipulation, the lever stop 32c (and possibly 32b also) can be passed through the lever-receiving opening 28, but upon different manipulation will cause the desired stop (illustrated in FIG. 3 as stop 32b) to be retained at the inside strap face 16. When the intended lever stop (32b for example, as illustrated) is retained against the strap inside face 16, pivoting the lever toward the outer strap end 30 will draw the defined band to a smaller circumference and tighten the strap against or around the underlying limb in question.

The stop 32a closest to the pivot 26 might be engaged to provide for the least band circumference reduction or pressure buildup against the limb, while the stop 32c furthest from the lever pivot 26 might be engaged to cause the most band reduction or pressure buildup, while stop 32b (or any other number of stops, not shown, between the closest stop 32a and furthest stop 32c from the pivot) might be engaged to provide for a band reduction or pressure buildup between the mentioned extremes. With the many lever-receiving openings 28 provided along the length of the strap, it is possible to select an appropriate opening that will define a band 14 of a size suited for encircling most any patient limb, even of vastly different sizes. Moreover, the user selection of one of the different stops 32 to have engaged against the strap provides for generating vastly different decrees of applied pressures.

When the lever 24 is inserted through a particular strap opening 28 and pivoted to be closely proximate and overlying the outside strap face 18 of the outer layer end 22, the lever opening 38 can be fitted over and interlocked with the post 34, to lock the medical band 8 in the tightened encircling position. However, most commonly prior to the lever being locked in position on the post, an nearby strap opening 36 can first be fitted over the locking post 34, serving to laterally hold the overlying strap ends together in the region underlying the lever, minimizing side-to-side shifting of the under and outer strap layer ends relative to one another.

It would be preferred to have a snap-lock construction at the free end of the post 34, effective to hold the lever firmly in place relative to the post after the lever has been closed tightly on the post, operable to lock the defined band device in place as applied on the patient. Nonetheless, appropriate forces intentionally and properly applied might open the lever from the post.

The strap 10 should be formed of a flexible but yet strong and slightly stiff material, such as nylon or another touch plastic, so that it can be pushed if needed under a partly raised patient, from one side of the patient to the other, to have the opposite strap ends accessible for engaging the securing apparatus 12 and tightening the endless band 14 around the patient's limb. The lever 24 should be significantly stiffer and of a strong durable material, again possibly of nylon or another touch plastic and possibly of a heavier gauge for needed stiffness to withstand the bending forces encountered during the tightening phase of securing the strap on the patient.

The medical band device 8 can be of a unitary assembly, making its use easy and reliable without needing or groping for separate components. If desired, the strap in the region of the pivot 26 might be reinforced or stiffened slightly to distribute the radial forces that would be applied against the patient under the lever pivot when pivoting the lever 24 to tighten the band over a wider area against the patient. The medical device 8 would be disposed after use.

The strap length must exceed the circumference of the limb to be wrapped and have overlapping opposite ends. The strap width should be sufficient (possible between one and three inches) to distribute the banding forces over the underlying skin without incurring patient pain or possible further injury. Although it would be possible to have a single model of the medical band device 8 that could work with the needs of most patients, it might be preferable to offer several models of the band device, varying in size (small and large) as might more specifically be suited for an appropriately sized limb and/or patient.

FIGS. 5–8 illustrate the use of two medical band devices 8 secured at spaced locations along a patient's arm or limb where rigid rods 48 might be connected to and between the spaced bands, operable to act then and an emergency splinting fixture 50. Sets of opposed clips 52, each having a housing 54 defining an open-ended bore 56 and a spaced retainer finger 58, might be snapped in place on and be secured to the bands in generally opposed and facing relationship. The ends of each separate rod 48 might be fitted into the respective clip bores 56. When the separate band devices 8 are tightened around the patient's limb, with the rods secured via the clips to the spaced bands, both rigidity and straightness might be provided to the limb between the spaced band devices, acting as an emergency splinting of the limb spanning for example a possible bone break therebetween.

While specific embodiments have been illustrated, it will be obvious that minor changes could be made therefrom without departing from the spirit of the invention. Accordingly, the invention is to determined by the scope of the following claims.

What is claimed is:

1. A medical device, comprising the combination of an elongated strap sized to fit around a patient's body area with overlapping opposite under and outer layer strap ends, and with an inside strap face adapted to lie proximate the patient and an opposite outside face;

means at the overlapping under and outer layer strap ends for securing the strap ends together to define an endless band effectively encircling the patient's body area;

said securing means including a lever pivoted relative to the outside face of the under layer strap end to swing about an axis disposed substantially perpendicular to the elongated axis of the strap;

structures on an intermediate part of the lever spaced apart along the lever from the lever pivot and structures on the outer layer strap end spaced apart along the strap, operable upon the engagement of different respective combinations of such structures for interlocking the lever and strap together differently;

whereby an appropriately selected lever-strap interlock engagement can be completed upon the lever being pivoted toward the strap inner layer end and the circumference of the band can then be reduced to a desired size and tightness upon the lever being pivoted in the opposite direction to a closed position proximate the strap under layer end; and means to hold the lever relative to the strap under layer end in the closed position.

2. A medical device according to claim 1, further wherein said means to hold the lever in the closed position comprises a post upstanding from the outside face of the under layer strap end at a location spaced from the lever pivot, and the lever having means suited to be releasibly interlocked with the post for holding the lever in the closed position.

3. A medical device according to claim 1, further wherein said structures on the outer layer strap end respectively comprise peripheral portions on the strap of separate spaced openings formed in the outer layer strap end, the lever being selectively inserted through one of the openings.

4. A medical device according to claim 1, further wherein said structures on the lever respectively comprise separate spaced stops formed on the lever and facing the outer layer strap end.

5. A medical device according to claim 1, further wherein said structures on the outer layer strap end respectively comprise peripheral portions on the strap of separate spaced openings formed in the outer layer strap end, the lever being selectively inserted through one of the openings, and said structures on the lever respectively comprise separate spaced stops formed on the lever and facing the outer layer strap end.

6. A medical device according to claim 5, further wherein said means to hold the lever in the closed position further comprises a post upstanding from the outside face of the under layer strap end at a location spaced from the lever pivot, and the lever having means suited to be releasibly interlocked with the post for holding the lever in the closed position.

7. A medical device according to claim 6, further wherein said means for holding the lever in the closed position comprises the lever having an opening formed in the lever spaced from the lever pivot and adapted to be fitted and locked in place onto the post.

8. A medical device according to claim 6, further wherein said strap has openings formed therein spaced apart along the outer layer end adapted to have one of said openings be inserted over the post prior to the lever being locked in place onto the post.

9. A medical device according to claim 1, further comprising the combination of having two of such devices secured around the patient's body area at spaced locations along the body area, respective sets of opposed clips held on the devices at spaced locations around the devices, and sets of rigid rods secured at opposite ends thereof relative to the respective sets of clips, operable for splinting the patient's body area between the devices.

\* \* \* \* \*